United States Patent [19]

Muetgeert et al.

[11] 4,418,147

[45] Nov. 29, 1983

[54] ENZYME IMMOBILIZATION IN A STARCH GEL

[75] Inventors: Johannes Muetgeert, Delft; Petrus H. L. Otto, De Lier; Frans A. Flippo, Delft, all of Netherlands

[73] Assignee: Nederlandse Organisatie Voor Toegepast-Natuurwetenschappelijk Onderzoek Ten Behoeve Van Nijverheid, Handel En Verkeer, The Hague, Netherlands

[21] Appl. No.: 337,303

[22] Filed: Jan. 5, 1982

Related U.S. Application Data

[63] Continuation of Ser. No. 94,055, Nov. 14, 1979, abandoned.

[30] Foreign Application Priority Data

Nov. 20, 1978 [NL] Netherlands ......................... 78.11417

[51] Int. Cl.$^3$ ..................... C12N 11/10; C12N 11/00; C12N 11/04
[52] U.S. Cl. .................................. 435/178; 435/174; 435/182
[58] Field of Search ................. 435/174, 178, 182, 94; 426/41

[56] References Cited

U.S. PATENT DOCUMENTS

| | | | |
|---|---|---|---|
| 3,223,593 | 12/1965 | Aldrich et al. | 435/178 |
| 3,838,007 | 9/1974 | Van Velzen | 435/181 X |
| 4,060,456 | 11/1977 | Long | 435/94 |
| 4,106,987 | 8/1978 | Kanno et al. | 435/94 |
| 4,126,706 | 11/1978 | Hilton | 426/516 X |
| 4,156,744 | 5/1979 | Kiploks et al. | 426/516 X |
| 4,163,691 | 8/1979 | Delos et al. | 435/174 |

FOREIGN PATENT DOCUMENTS

| | | |
|---|---|---|
| 7114315 | 4/1972 | Netherlands . |
| 1306752 | 4/1973 | United Kingdom . |
| 1359666 | 7/1974 | United Kingdom . |

OTHER PUBLICATIONS

Dahlquist et al., Hydrolysis of B-Galacto Sides Using Polymer Entrapped Lactase, Biotechnology and Bioengineering, vol. XV, 1973.

Guilbault et al., Immobilization of Cholinesterase and Urease, Anal. Biochem., vol. 33, 1970 (pp. 341–355).

Enzymes May Milk Dairy Wastes, Chemical Week 1977 (pp. 37–38).

Mosbach K., Immobilized Enzymes, Methods in Enzymology, vol. XLIV, 1976 (pp. 652–653).

Bauman et al., Preparation of Immobilized Cholinesterase for Use in Analytical Chemistry, Anal. Chem., vol. 37, No. 11, 1965 (pp. 1378–1371).

Goodson et al., An Immobilized Cholinesterase Product for Use in the Rapid Detection of Enzyme Inhibitors in Air or Water, Analytical Biochemistry, vol. 51, 1973 (pp. 362–367).

*Primary Examiner*—David M. Nafe
*Attorney, Agent, or Firm*—Brumbaugh, Graves, Donohue & Raymond

[57] ABSTRACT

Cell-free enzymes are immobilized by mixing the enzymes with a starch sol or a partially gelled starch gel to form a mixture containing preferably 20 to 60% starch, gelling the mixture, extruding the gelled mixture to form strands, drying the strands and breaking the dried strands into pieces to form shaped structures having improved mechanical strength.

17 Claims, No Drawings

ENZYME IMMOBILIZATION IN A STARCH GEL

This is a continuation, of application Ser. No. 094,055 filed Nov. 14, 1979, now abandoned.

The present invention concerns an immobilized enzyme, processes for the preparation of said enzyme as well as a process for carrying out an enzymatic reaction using the immobilized enzyme according to the invention.

It is known to combine enzymes with a carrier, said carrier being insoluble in the medium in which the enzyme has to be used. The aim of the immobilization of enzymes is to obtain an enzyme product which can be separated easily from the reaction medium and can be reused as a biochemical catalyst. Several chemical as well as physical methods are known for fixing an enzyme to an insoluble carrier. For example, the enzyme can be bound to a carrier by way of covalent chemical bonds. In that case the carrier contains active groups which may be introduced separately, said active groups reacting with one or more active groups of the enzyme. Activated polysaccharides, synthetic polymers and activated inorganic carriers have been suggested as active carrier materials. It is also known that an enzyme can be coupled with a carrier by way of a bifunctional cross-linking agent. For example, glutaric aldehyde is known as a cross-linking agent. As representative physical methods for fixing an enzyme to a carrier the following may be mentioned: the fixation to an ion exchange resin, encapsulation in microcapsules, entrapment in fibres of synthetic polymers and occlusion in natural or synthetic gels.

When the immobilized enzymes have to be used for the preparation of an edible product, the methods for immobilization using a chemical cross-linking agent and/or synthetic polymers are usually not very desired because the chemical cross-linking agents as well as the chemicals, used for the preparation of the synthetic polymers, are not completely harmless. Now the invention provides an immobilized enzyme the ingredients of which are harmless to human beings and animals.

It has been proposed to immobilize an enzyme by entrapping it in a starch gel. This proposal has been described in the U.S. Pat. No. 3,223,593. For this purpose a clear, viscous sol is prepared by heating 3.25 g of a special starch (Connaught starch) and 25 ml of distilled water. The cooled sol is mixed with a solution of horse serum cholinesterase, after which the whole composition is allowed to gel. According to a publication in Anal. Chem. 37 (1965), page 1378–1381, the gel has only a small mechanical strength and therefore it is proposed in this article to take up the gel into a pad of polyurethane foam with open pores. Also the fixation of the enzyme to the gel leaves much to be desired, because about 15% of the enzyme is washed out easily.

According to the U.S. Pat. No. 4,106,987 glucose isomerase fixed to microbial cells is immobilized in a natural water-insoluble gel forming substance. As one of the applicable gel forming substances starch is mentioned.

Surprisingly it appeared that also cell-free enzymes can be immobilized excellently in a starch gel. Therefore an object of the invention is to provide an immobilized enzyme comprising shaped structures of a dried starch gel in which one or more cell-free enzymes are occluded.

Preferably the immobilized enzyme according to the invention is in particulate form. The product has a surprisingly good mechanical strength. The enzyme content can be adjusted at any value desired, provided that the starch gel can retain the enzyme. Generally the amount of enzyme which can be taken up in the starch gel and can be retained by the starch gel, is at the most 15%, calculated on the weight of the starch.

Another object of the invention is a process for preparing an immobilized enzyme wherein one or more enzymes are taken up in a starch gel. Said process is characterized by mixing an at most partially gelled starch sol having a starch content of 20–60% by weight with the enzyme, allowing the mixture to gel, and bringing it into the form of dried shaped structures.

In practice first a starch sol is prepared by kneading the starch with water at a high temperature. Then the sol is cooled to a temperature at which the enzyme(s) to be added does not decompose, after which the sol, that may be gelled at most partially, is immediately mixed with the enzyme. After that the mixture obtained is allowed to gel. Desirably, the mixing with the enzyme is carried out at the highest possible temperature to prevent an early gelling of the mixture.

A very favorable method by which the gelled enzyme containing mixture can be formed into dried shaped structures consists of extruding the mixture to strands, drying the strands and then reducing said strands to pieces. In this way a particulate product having a great mechanical strength is produced. This property is maintained when the product is contacted with an aqueous liquid.

The drying may be carried out in the air or under reduced pressure, at high temperature but not that high that deactivation of the enzyme occurs. Generally the drying may be carried out safely t temperatures below 30° C.

Although any natural starch, such as corn, wheat, rye, tapioca, cassava, rice, potato or buckwheat starch, or starches from Leguminosae may be used as a starch in the immobilized enzyme products according to the invention, also pure starch fractions separated from said starches, such as amylopectin (the branched starch fraction) may be used. It is also possible to use starch derivatives allowing the preparation of a sol having a content of 20–60% by weight, said sol not gelling completely in a short time at the maximum temperature at which it can be mixed with the enzyme (the decomposition temperature of the enzyme). Preferably the starch is potato starch or amylopectin obtained from potato starch or corn starch.

The invention may be used to immobilize various enzymes, such as lactase, invertase, catalase, glucose-oxidase, phosphoglucose-oxidase, aminoacylase, orthophosphoric acid mono-ester phosphohydrolase and the like. Very good results have been obtained with lactase, catalase, glucose-oxidase, and a combination of catalase and glucose-oxidase.

Furthermore, it was surprisingly found that the enzyme occluded in a starch gel according to the invention can be purified very easily by extracting the immobilized enzyme with water or a salt solution, e.g. a buffer solution.

For that purpose the granulates of the immobilized enzyme can be suspended in the extraction liquid and the suspension can be stirred gently. Then the immobilized enzyme can be sucked off and if necessary, the process can be repeated several times. As an extraction liquid, a 0.02 M potassium phosphate buffer of pH 7.0 is particularly suitable. It appeared that by using this extraction process a large amount, in the case of lactase as much as 75%, of the original nitrogen content being present in the immobilized enzyme can be removed without decrease of the enzyme activity. This was the case with a commercially available enzyme preparation obtained from *Saccharomyces lactis.*

This possibility for purifying the enzyme preparation in a simple way is extremely important, because according to the invention rather impure enzymes, having a lower cost than purified enzymes, may be used as starting materials.

The immobilized enzymes according to the invention are extremely well suited for carrying out enzymatic reactions and therefore the use of the immobilized enzymes according to the invention and the use of an immobilized enzyme prepared according to the invention form part of the invention.

An important application of one of the immobilized enzymes according to the invention, viz. immobilized lactase, is the treatment of milk having a normal or reduced fat content or treatment of whey, to convert the lactose present therein into a mixture of glucose and galactose. Particularly in case of products to be consumed by human beings or animals it is undesirable to add the enzyme in a soluble form because in that case the enzyme remains in the product. As indicated above chemical, generally toxic auxiliary substances, i.e. bifunctional reagents such as dialdehydes, carbodiimide, epoxides and the like are required for the enzyme immobilization (U.S. Pat. No. 3,838,007). On the other hand, enzyme preparations which are physically or chemically occluded in gels, e.g. polyacrylamide gel (Biotechnical and Bio-Engineering 15, 395–402 (1973)), by polymerization in situ, remain polluted by residues of the chemical catalysts required for the polymerization such as radical initiators and other low-molecular and also toxic reaction accelerators. The immobilized lactase products according to the invention do not have such disadvantages because said products have been prepared from harmless products only.

Another advantage of the immobilized lactase according to the invention is that the effectiveness of said lactase hardly decreases by using it. Not only is the enzyme very strongly fixed to the starch, but also the hydrolysis of lactose can be carried out in such a way that the immobilized enzyme will not be impaired by clogging of the pores by deposition of milk proteins and other milk ingredients on the carrier particles. This disadvantage does occur with the known immobilized enzymes (Chemical Week, Nov. 14, 1977, page 37-38). It is found that the particles can be allowed to abrade without being disintegrated. In this way the surface of the particles is cleaned and an extra diffusion resistance, possibly caused by pollution, is avoided. Such a very slow abrasion process may be accomplished by stirring the contents of a reactor containing the mixture of enzyme catalyst particles and substrate (e.g. lactose containing liquid), or by keeping the enzyme catalyst particles in a fluidized state by an upward of stream liquid. By controlling the energy introduced by stirring or fluidization, respectively, the desired abrasion rate can be obtained easily and the deposition of milk proteins or other polluting deposits can be avoided efficiently.

Invertase or β-fructosidase is an enzyme which can be produced by certain strains of *Saccharomyces cerevisiae.* The enzyme may be used for preparing fructose from saccharose and/or maltose. It appears that in the immobilized form according to the invention invertase is also fixed very strongly to the starch gel. The invertase activity is not reduced after storage in a buffer of pH 5.2 in a refrigerator during 40 days. Also the immobilized enzyme may be used for saccharose inversion at a higher temmperature, e.g. 40° C., without affecting the activity. At this higher temperature the inversion reaction proceeds considerably faster. When an impure enzyme has been used in immobilized enzyme it is possible to wash out a considerable amount of impurities without reducing the invertase activity.

Catalase may be isolated from cow liver and may be used for the elimination of hydrogen peroxides used as a disinfectant. Hydrogen peroxide for disinfection purposes may be produced by using an immobilized glucose-oxidase according to the invention, after which the remaining amount of hydrogen peroxide may be eliminated with a catalase immobilized according to the invention. Catalase as well as glucose-oxidase are very strongly fixed to the starch gel.

A very important application of the present enzyme preparations lies in the elimination of oxygen from glucose containing liquids such as beer and other beverages. The presence of oxygen in beer is undesirable because it may cause an unfavorable change of the taste. For the elimination of oxygen from glucose containing beverages a catalase and glucose-oxidase containing immobilized enzyme according to the invention may be used successfully. It is also possible to produce gluconic acid from glucose with a catalyst containing said enzymes, by introducing oxygen.

The following examples illustrate the invention.

EXAMPLE I 80 g air dry native potato starch (moisture content 17% by weight) and 100 g of a 0.02 M potassium phosphate buffer of pH 7.0 are introduced in an double walled trough of a stainless steel Werner Pfleiderer laboratory kneader provided with sigma-shaped kneading means. Under continuous kneading the contents of the kneader is heated at 96° C. by heating with boiling water by way of the double wall. At this temperature the kneading is continued during one hour. Then in about 30 minutes, the mixture is cooled to 27° C., after which a solution of 3.5 g of a lactase preparation obtained from *Saccharomyces lactis* in 16.5 g of a 0.02 M potassium phosphate buffer of pH 7.0 is added. The whole mixture is kneaded at room temperature during one hour and then the contents of the kneader are transferred to a glass vessel which is closed and stored during about 16 hours at a temperature of 4° C.

The next day strands are produced at 20° C. with the aid of a stainless steel extruder provided with a plate having holes of a diameter of 1.0 mm. Then the extruded strands are dried during 6 hours at 25°–28° C. in a drying stove with air circulation to obtain a moisture content of about 13% by weight. Grinding during a short time in an impact mill and screening produces granulates consisting of cylindrical particles having a diameter of 0.9 mm and a length of 0.4–1.2 mm. The granulates have a light brown color and a moldy odor.

EXAMPLE II

As described in Example I a mixture of 110 g of air dry amylopectin (moisture content about 11% by weight) and 110 g of a 0.02 M potassium phosphate buffer of pH 7.0 is kneaded during 60 minutes at 85°–90°

C. After cooling to 30° C. a solution of 5.0 air dry lactase preparation obtained from *Saccharomyces lactis* (moisture content about 11% by weight) in 25.0 g. of a 0.02 M phosphate buffer (pH=7.0) is added. Then the mixture is kneaded during one hour at 25° C. and subsequently left alone during 16 hours at 4° C.

Extrusion, drying, grinding and screening according to Example I results in similar granulates as in Example I.

EXAMPLE III

As described in Example I a mixture of 97 g air dry potato starch (moisture content 17.2% by weight) and 78 g of a 0.02 M potassium phosphate buffer (pH=7.0) is kneaded under heating. After reaching a temperature of 96° C. the kneading is continued during one hour at 96° C. Then coding to 28° C. is effected in about 30 minutes whereupon a solution of 4.0 g air dry lactase from *Saccharomyces lactis* (moisture content about 8.5% by weight) in 25.0 g of a 0.02 M potassium phosphate buffer pH 7.0 is added to the contents of the trough. Then the mixture is kneaded during one hour at 28–22° C. and subsequently stored in a closed glass vessel during 16 hours at 4° C.

Extrusion, drying, grinding and screening according to Example I results in similar granulates as in Example I.

EXAMPLE IV

Purification of the enzyme catalyst of Example II.

In a closed reaction vessel of glass, provided with a stirrer, 100 g of the enzyme granulates obtained according to Example II, and 800 g of 0.02 M potassium phosphate buffer in double-distilled water of pH 7.0 is agitated by gently stirring during 7 hours. Then the stirring is stopped, the supernatant is sucked off, whereupon the described treatment is repeated twice with fresh portions of 800 g of the washing liquid. The so obtained granulates, saturated with buffered water, are directly suited for hydrolytic splitting of lactose in aqueous systems. In swollen as well as in dry condition this material is a colorless, tasteless and odorless product.

It appeared that in said dry condition (moisture content about 11–13%) the product remains unchanged for at least three months when stored at a temperature of about 4° C. During the storage period the specific activity remains identical to the initial value of the freshly produced preparation.

EXAMPLE V

Hydrolysis of lactose using the pre-washed swollen enzyme catalyst granulates of Example IV Substrate: a solution of chemically pure lactose monohydrate in 0.02 M potassium phosphate buffer in double-distilled water of pH 7.0 also containing 2.0 mM magnesium sulphate per liter. This solution contains per 100 ml 5.28 g lactose, calculated on the anhydrous product.

In a stirred glass rector are introduced:
 1800 g of the substrate liquid
 300 g of the swollen catalyst granulates (containing only 100 g air dry catalyst material, in which 5.0 g of air dry enzyme preparation have been taken up).

The lactose concentration decreases to 4.75 g of anhydrous lactose per 100 ml by adding the catalyst. While continuously, but moderately fast stirring the decrease of the lactose content with time at 25° C. is followed by means of an automatic oxidimetric analysis.

The results observed during a reaction time of 60 minutes are summarized in Table A.

TABLE A

Hydrolysis of lactose in water under the influence of β-galactosidase (lactase) in an amylopectin gel.

| Elapsed time in minutes | Converted lactose in % of the initial lactose |
|---|---|
| 0 | 0 |
| 10 | 23 |
| 30 | 58 |
| 60 | 82 |

After an hydrolysis of one hour, a lactose content sufficiently low for application in the dairy industry has been achieved. The catalyst mass was removed from the substrate liquid by filtration, the catalyst was washed twice with portions of 100 ml of double distilled water, buffered with potassium phosphate at pH=7.0 and after sucking off the final washing, the immobilized enzyme was mixed again with 1800 g of fresh lactose solution.

This procedure was repeated 20 times and it was found that the hydrolysis results of Table A remained almost unchanged, even after the twentieth repetition.

After the twentieth repetition the catalyst was washed and dried until a constant weight was achieved. A loss of weight of 6% with regard to the initial weight of the catalyst had occurred due to mechanical "abrasion" or "dissolution" respectively.

EXAMPLE VI

As described in Example V hydrolysis tests were carried out using the enzyme granulates obtained according to Example I. 2.0 g air dry enzyme granulates according to Example I per 40.0 g of 4.75% aqueous lactose solution of pH=7.0 and a temperature of 25.0° C. were used.

After every run the catalyst mass was filtered off, the catalyst was washed in the same way as in Example V and then reused for the next run. The results are given in Table B.

TABLE B

| | Degree of hydrolysis | |
|---|---|---|
| Run No. | % Converted lactose after 10 minutes | % Converted lactose after 30 minutes |
| 1 | 20 | 48 |
| 2 | — | 57 |
| 3 | 25 | 60 |
| 4 | 29 | 60 |
| 5 | 29 | 59 |
| 6 | — | — |
| 7 | — | 58 |
| 8 | 26 | 58 |
| 9 | 27 | 58 |
| 10 | 26.5 | 58 |

After the tenth run the enzyme granulates were separated and contacted again with 40.0 g of the 4.75% lactose solution. The whole composition was allowed to stand for 288 hours. After this period is appeared that the enzyme granulates had the same activity as the value of run No. 10.

EXAMPLE VII

As described in Example V hydrolysis tests were carried out using the enzyme granulates according to Example III. 4.0 g air dry enzyme granulates according to Example III were suspended under moderately fast stirring in 80.0 g of a 4.75% solution of lactose in 0.02 M potassium phosphate buffer pH 7.0.

After a contact time of 10, 30 and 60 minutes at a temperature of 25° C. the amount of converted lactose was determined by means of an oxidimetric automatic analysis. The degree of reaction or hydrolysis was expressed as the percentage of converted lactose. After a contact time of one hour the substrate liquid was separated from the enzyme granulates by decantation.

Then the enzyme granulates were washed twice during about 15 minutes with portions of 70 g of 0.02 M potassium phosphate buffer of pH 7.0 and then suspended again in a fresh lactose solution. Subsequently the same measurements were carried out again.

During five consecutive days 4 measurement series per day were carried out. The results are summarized in Table C.

TABLE C

Hydrolysis of lactose in water under the influence of lactase in a potato starch gel.

| Reaction time in minutes | Degree of conversion in % of the initial present lactose after the $n^{th}$ repetition. | | | | | |
|---|---|---|---|---|---|---|
| | n = 0 | n = 3 | n = 6 | n = 10 | n = 15 | n = 19 |
| 10 | 18.0 | 28.5 | 31.0 | 30.0 | 26.0 | 25.5 |
| 30 | — | 61.0 | 64.0 | 62.0 | 57.0 | 57.0 |
| 60 | 74.0 | 83.0 | 86.0 | 82.0 | 82.0 | 83.0 |

After the twentieth measurement the catalyst was washed with the buffer until a constant weight was obtained and by weighing it was determined that about 4.2% of the original weight of the granulates was lost due to "abrasion".

EXAMPLE VIII

Hydrolysis of lactose in sterilized skim milk at 25° C.

Substrate: "Lilac" milk (Belgium) sterilized at high temperature; lactose content: 4.8 g per 100 ml.

Test equipment; procedure and analysis were fully identical with those of Example V. In this example a series of repeated measurements with the same initial enzyme preparation was carried out. In total twenty hydrolyses was carried out. The results are summarized in Table D.

TABLE D

Hydrolysis of lactose in skim milk at 25° C., under the influence of β-galactosidase occluded in an amylopectin gel.

| Reaction time in minutes | Degree of conversion of lactose in % of the originally present lactose after the $n^{th}$ repetition. | | | | | |
|---|---|---|---|---|---|---|
| | n = 0 | n = 1 | n = 4 | n = 8 | n = 12 | n = 20 |
| 0 | 0 | 0 | 0 | 0 | 0 | 0 |
| 10 | 16.3 | 15.6 | 16.1 | 14.8 | 14.9 | 12.1 |
| 30 | 42.5 | 42.0 | 43.0 | 40.0 | 42.0 | 37.0 |
| 60 | 58.0 | 56.0 | 56.8 | 56.0 | 53.0 | 49.0 |
| 120 | 78.0 | 76.0 | 75.7 | 72.0 | 71.2 | 64.0 |

EXAMPLE IX

Preparation of immobilized invertase.

As described in Example I a mixture of 40.0 g air dry amylopectin (moisture content about 13% by weight) and about 50 ml of 0.02 M potassium phosphate buffer (pH 5.2) was kneaded during one hour at 90° C. and then cooled to about 40° C. Subsequently a solution of 0.8 g invertase in about 9 ml water was added. Then, under continued cooling to 25° C., the mixture was kneaded during one hour and further stored in a refrigerator (about 5° C.) during 16 hours.

The mixture was extruded in the same way as in Example I, with the difference that a plate having holes of 0.5 mm was used. The extruded product was dried in an oven with air circulation, then ground and screened to obtain a fraction having the desired particle size of about 0.3–0.6 mm.

EXAMPLE X

According to Example V the invertase activity of the immobilized invertase prepared according to Example IX was measured. The amount of glucose and fructose formed was measured by means of an automatic oxidimetric analysis. The measurements were repeated several times. Between the measurements the enzyme preparation was stored at 5° C. in 0.02 M potassium phosphate buffer, pH 5.2. A series of tests were carried out at 25° C. and at 40° C. The results are given in Table E.

TABLE E

Inversion of saccharose.
Enzyme preparation: according to Example IX.
Substrate: 5.4% by weight of saccharose
in 0.02 M phosphate buffer, pH 5.2.
Weight ratio enzyme preparation:substrate = 1:80

| Storage period prior to the measurement (days) | Degree of conversion of saccharose in % of originally present saccharose | | | |
|---|---|---|---|---|
| | reaction at 25° C. | | reaction at 40° C. | |
| | after 10 min. | after 30 min. | after 10 min. | after 20 min. |
| 1/4 | 27.0 | 62.0 | 45.0 | 75.0 |
| 1/2 | 30.0 | 62.0 | 50.0 | 80.0 |
| 2/3 | 28.0 | — | 50.0 | 75.0 |
| 1 | 26.0 | 59.0 | 47.0 | 72.0 |
| 2 | 25.5 | 60.0 | — | — |
| 40 | 28.0 | 61.0 | — | — |

From these tests it appears that the immobilized invertase keeps its activity even after a prolonged use and also can be used at a higher temperature (40° C.).

EXAMPLE XI

A. Preparation of immobilized catalase

In a laboratory model Werner-Pfleiderer kneader the following materials were brought together:
80 g of air dry amylopectin
90 g 0.05 M potassium phosphate buffer of pH 5.6 and kneaded during one hour at 90° C.

After cooling to 20° C. the following was added to the homogeneous mass: 30 g of a solution obtained by dissolving of dispersing 2.5 g of catalase (Sigma $C_{10}$ with an activity of 3400 Sigma-units) in 27.5 g of 0.05 M potassium phosphate buffer of pH 5.6.

Then the kneading was continued during one hour. After that the preparation was stored in a closed vessel during 16 hours at 5° C. and then, after extrusion to form strands with a diameter of 0.5 mm, dried and reduced by grinding to form granulates consisting of cylindrical particles having a diameter of 0.45 mm and a length of 0.3–0.6 mm. The air dried product contained about 100 units catalase activity per mg.

B. Determination of loss of activity of washing

Determination of enzyme loss by means of electrometric measurement of oxygen freed by reaction of the used washing liquid with a 0.04% aqueous hydrogen peroxide solution.

50 mg of the enzyme product obtained according to A were shaken for 15 minutes with 2.0 ml of 0.7 M potassium phosphate buffer pH 7.1. After decantation the clear washing liquid was poured off and the catalase activity in said liquid was measured by allowing the washing liquid to react with a 0.04% hydrogen peroxide solution at 25.0° C. and measuring the production of oxygen with an oxygen electrode. This procedure was carried out 15 times using always the same sample of 50 mg of immobilized catalase. After 6 washings a total loss of 35.3 units of activity appeared, i.e. only 0.7% of the originally present catalase activity. The losses after the sixth washing were negligible.

EXAMPLE XII

A. Preparation of immobilized catalase/glucose-oxidase

In a laboratory model Werner Pfleiderer kneader the following materials were brought together:
79 g of air dry amylopectin
100 g of 0.01 M phosphate buffer pH 5.6 and kneaded during one hour at 90° C.

After cooling to 36° C. the following was added to the homogeneous mass:
21 g of a solution obtained by dissolving in or mixing with 20 g of 0.01 M phosphate buffer pH=5.6:
0.100 g of glucose-oxidase (Boehringer Grade I; activity 200 U/mg) and
1.00 g of catalase solution (Boehringer No. 106836; 260,000 U/ml).

Under continuous cooling the mixture was kneaded during one hour achieving a final temperature of 30° C. The mixture obtained was stored during 16 hours at 6° C.; then the gel obtained was extruded to form strands having a diameter of 0.5 mm, the strands were dried using a stream of air of 30° C. and finally ground to form grains having a length of about 0.5 mm.

B. Washing procedure: determination of loss of enzyme by measurement of the activity of the wash water; homogeneous catalysis 4.0 g of the air dry product (moisture content about 10% by weight) prepared according to A and having glucose-oxidase content of about 0.125% by weight were shaken during different times with portions of 30 g of about 0.005 M phosphate buffer pH 5.6. After decantation, washing twice the residue with portions of 25 ml of a fresh buffer solution and combining 11 washing liquids the total glucose-oxidase activity of the washing liquids was determined. By repeating this washing procedure with the same material the results stated in Table F were obtained.

TABLE F

| Washing No. | Loss of enzyme by washing | | |
|---|---|---|---|
| | Time in hours | Temperature in °C. | Loss of enzyme in mg[xxx] |
| 1[x] | 0.75 | 22 | 0.08 |
| 2[x] | 3 | 22 | 0.06 |
| 3[xx] | 16 | 6 | 0.05 |
| 4[x] | 4 | 22 | 0.02 |
| 5[xx] | 40 | 6 | 0.02 |
| 6[x] | 6 | 22 | 0.02 |
| 7[xx] | 90 | 6 | 0.02 |

[x]stirred with buffer solution
[xx]standing in buffer solution at 6° C.
[xxx]calculated from the measured activity in the washing liquid.

Therefore the total loss of enzyme is less than 0.27 mg or 5.4% of the total amount.

C. Application of the immobilized enzymes for elimination of oxygen from a 0.5% glucose solution Analysis method 0.200 g of the immobilized enzymes, washed according to B were introduced in a glass reaction vessel of 32.0 ml, kept at 25.0° C. in a thermostat, and provided with:
a. a magnetic stirrer
b. a "Clark" oxygen electrode and
c. a glass capillary for gas supply and an aqueous 0.02 M sodium acetate buffer of pH 4.59 was added to obtain a total volume of 32.0 ml.

Then air of atmospheric pressure was passed through the capillary while recording the oxygen uptake by means of the Y.S.I. "Biological Oxygen Monitor" (Yellow Springs Instrument Co., Inc.) provided with a recorder and connected to the Clark electrode. When the saturation concentration was reached the instrument was adjusted to 100% saturation, after which nitrogen was passed through under atmospheric pressure until the saturation value was reduced to 50%. Then the amount of dissolved oxygen is about 0.14 millimole per liter or about 4.4 mg per liter.

Then 0.5 ml aqueous, oxygen-free, 32% glucose solution was injected in the vessel through the capillary at the same time pressing out 0.5 ml of the buffer solution (runs off through the capillary). The oxygen decrease which commenced immediately was registered against time using the connected recorder. As soon as the total amount of oxygen had been consumed, the glucose solution was decanted from the reaction vessel, the enzyme preparation was washed four times with portions of 15 ml of fresh, glucose-free buffer solution and the test was repeated.

This procedure was repeated totally five times. After 15 minutes it appeared that about 20% of the saturation concentration of oxygen was present, while after 30 minutes the solution was almost oxygen-free. No decrease of activity was found.

EXAMPLE XIII

Elimination of oxygen from beer

According to the method described in Example III 32 ml of beer ("Heineken Oud Bruin"), the oxygen content of which was adjusted to 6.5 mg per liter, were treated with 200 mg of the enzyme product obtained according to Example XII(A). The results obtained are given in Table G.

TABLE G

| Oxygen content of beer after treating with immobilized glucose-oxidase/catalase at 25° C. | | | |
|---|---|---|---|
| Minutes | mg $O_2$/l | minutes | mg $O_2$/l |
| 3 | 5.85 | 18 | 1.43 |
| 6 | 5.01 | 21 | 0.91 |
| 9 | 3.97 | 24 | 0.49 |
| 12 | 2.99 | 27 | 0.20 |
| 15 | 2.15 | 30 | 0.10 |

As appears from Table G after 24 minutes an oxygen concentration acceptable for beer is achieved, while already after 30 minutes almost oxygen-free beer (<0.1 mg/l) is obtained.

EXAMPLE XIV

Formation of gluconic acid from glucose

Action of 400 mg of the immobilized enzymes obtained according to Example XII(A) upon an aqueous, 0.9% glucose solution buffered with 0.005 M potassium phosphate at pH 5.6, while continuously passing through oxygen under atmospheric pressure.

The production of gluconic acid appeared from the consumption of a 0.1 N sodium hydroxide solution registered by means of the recorder of an automatically dosing titration device, while keeping the pH constant.

It appears that per hour about 4% of the originally present glucose is converted into the equivalent amount of gluconic acid.

We claim:

1. An immobilized enzyme consisting of a starch gel, occluding one or more cell-free enzymes, wherein said starch gel is formed by mixing one or more cell-free enzymes with a starch sol or a partially gelled starch gel, said mixture having a starch content of 20–60% by weight, whereupon said mixture gels and the gelled mixture is extruded into strands and said strands are dried and broken into pieces to form shaped structures.

2. Immobilized enzyme according to claim 1 having the form of granulates.

3. Immobilized enzyme according to claim 1 or 2 having maximum enzyme content of 15% by weight.

4. Immobilized enzyme according to claim 1 wherein the enzyme is selected from the group consisting of lactase, invertase, catalase, glucose-oxidase, phosphoglucose-oxidase, aminoacylase, ortho-phosphoric acid mono-ester phosphohydrolase and a combination of catalase and glucose-oxidase.

5. Immobilized enzyme according to claim 1 wherein the starch is selected from the group consisting of potato starch and amylopectic obtained from potato starch or corn starch.

6. Immobilized anzyme according to claim 5 wherein the starch is the amylopectin.

7. Immobilized enzyme according to claim 4 wherein the enzyme is selected from the group consisting of lactase, catalase, glucose-oxidase and a combination of catalase and glucose-oxidase.

8. A process for preparing an immobilized enzyme by occluding one or more enzymes in a starch gel, which comprises mixing a starch sol or a partially gelled starch gel having a starch content of 20–60% by weight with the enzyme, allowing the mixture to gel, extruding the gelled mixture to form strands, drying the strands and breaking the dried strains into pieces to form shaped structures.

9. The process according to claim 8 wherein the enzyme is selected from the group consisting of lactase, invertase, catalase, glucose-oxidase, phosphoglucose-oxidase, aminoacylase, orthophosphoric acid mono-ester phosphohydrolase and a combination of catalase and glucose-oxidase.

10. The process according to claim 8 wherein the starch is selected from the group consisting of potato starch and amylopectin obtained from potato or corn starch.

11. The process according to claim 10, wherein the starch is the amylopectin.

12. The process according to claim 9 wherein the enzyme is selected from the group consisting of lactase, catalase, glucose-oxidase and a combination of catalase and glucose-oxidase.

13. The process according to claim 8 further comprising the step of purifying the immobilized enzyme by extracting the same with water or a salt solution.

14. The process according to claim 13, wherein the salt solution is a buffer solution.

15. The process according to claim 14, wherein the buffer solution is a 0.02 M potassium phosphate buffer.

16. The process according to claim 15 wherein the enzyme is purified by extracting with a 0.02 M potassium phosphate buffer pH 7.0.

17. In a process for carrying out an enzymatic reaction, the improvement comprising the step of using therein the immobilized enzyme prepared according to claim 8.

* * * * *

UNITED STATES PATENT AND TRADEMARK OFFICE
CERTIFICATE OF CORRECTION

PATENT NO. : 4,418,147

DATED : November 29, 1983

INVENTOR(S) : Muetgeert et al.

It is certified that error appears in the above-identified patent and that said Letters Patent is hereby corrected as shown below:

First page, col. 2, line 8, after "1973" insert --(pp. 395-402)--;

First page, col. 2, line 17 "1371" should read --1381--;

Col. 2, line 36 "t" should read --at--;

Col. 5, line 1, "5.0" should read --5.0 g--;

Col. 5, line 17, "coding" should read --cooling--;

Col. 6, line 61, "is" should read --it--;

Col. 7, line 44, "was" should read --were--;

Col. 8, line 52, "of" should read --or--;

Col. 8, line 63, "of washing" should read --by washing--;

UNITED STATES PATENT AND TRADEMARK OFFICE
CERTIFICATE OF CORRECTION

PATENT NO. : 4,418,147

DATED : November 29, 1983

INVENTOR(S) : Muetgeert et al.

It is certified that error appears in the above-identified patent and that said Letters Patent is hereby corrected as shown below:

Col. 10, line 12, "and an aqueous ..." should start a new line;

Col. 11, line 37, "amylopectic" should read --amylopectin--;

Col. 11, line 39, "anzyme" should read --enzyme--;

Col. 12, line 9, "strains" should read --strands--.

Signed and Sealed this

Tenth Day of April 1984

[SEAL]

Attest:

GERALD J. MOSSINGHOFF

Attesting Officer

Commissioner of Patents and Trademarks